US006696052B2

(12) United States Patent
Aeby et al.

(10) Patent No.: US 6,696,052 B2
(45) Date of Patent: Feb. 24, 2004

(54) HAIR CARE COMPOSITIONS WITH DIQUATERNARY SILICONE POLYMERS

(75) Inventors: Johann Aeby, Marly (CH); Bernhard Irrgang, Menziken (CH); Herbert Mager, Marly (CH); Gilbert Pasquier, Praroman (CH); Emmanuel Romanens, Posieux (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/056,307

(22) Filed: Jan. 24, 2002

(65) Prior Publication Data

US 2002/0146381 A1 Oct. 10, 2002

(30) Foreign Application Priority Data

Jan. 31, 2001 (DE) .......................... 101 04 033

(51) Int. Cl.[7] ............................... A61K 7/075
(52) U.S. Cl. .............................. 424/70.122; 424/70.19; 424/70.27; 424/70.28
(58) Field of Search ................... 424/70.1, 70.122, 424/70.19, 70.27, 70.28

(56) References Cited

U.S. PATENT DOCUMENTS

| 5,306,434 A | 4/1994 | Schueller et al. |
| 5,328,685 A | 7/1994 | Janchitraponvej |
| 5,556,615 A | 9/1996 | Janchitraponvej |
| 6,136,304 A | 10/2000 | Pyles |

FOREIGN PATENT DOCUMENTS

| DE | 35 27 974 A1 | 2/1987 |
| EP | 0 284 036 A2 | 9/1988 |
| EP | 0 550 361 A1 | 7/1993 |
| EP | 0 636 356 A1 | 2/1995 |
| EP | 0 669 391 A2 | 8/1995 |
| EP | 0 614 349 B1 | 2/1996 |
| EP | 0 689 532 B1 | 5/1997 |
| WO | 9603970 A1 | 2/1996 |
| WO | 00/45787 | 8/2000 |

OTHER PUBLICATIONS

Johnson, D..H (HRSG): "Hair And Hair Care", New York, 1997, pp. 65–104.

Primary Examiner—Jyothsna Venkat
(74) Attorney, Agent, or Firm—Michael J. Striker

(57) ABSTRACT

The hair care compositions contain a combination of from 0.01 to 10 percent by weight of at least one terminally functionalized diquaternary silicone compound of formula II:

$$R^1R^2R^3N^+\!-\!A\!-\!SiR^7R^8\!-\!(O\!-\!SiR^9R^{10})_n\!-\!O\!-\!SiR^{11}R^{12}\!-\!A\!-\!N^+R^4R^5R^6{}_2X^{1-} \quad (II),$$

wherein $R^1$ and $R^4$, independently of each other, each represent an alkyl group with at least eight carbon atoms, and $R^2$ $R^3$ and $R^{15}$ to $R^4$, independently of each other, each represent a methyl group. A represents —$(CH_2)_3$—O—$CH_2$—$CH(OH)$—$CH_2$—, n is a number from 10 to 120 and $X^{1-}$ is an anion; and from 0.01 to 10 percent by weight of at least one quaternized amine compound of formula lb:

$$R1\!-\!NH\!-\!(CH_2)_m\!-\!N^+R2R3R4\ X^- \quad (lb)$$

wherein R1 represents a C8- to C24-acyl group; wherein R2, R3 and R4 represent, independently of each other, C1- to C6-alkyl group; $X^-$ is an anion and m is 2 to 5. These compositions optionally contain at least one ester of an alphatic carboxylic acid with a primary or secondary alcohol.

6 Claims, No Drawings

HAIR CARE COMPOSITIONS WITH DIQUATERNARY SILICONE POLYMERS

BACKGROUND OF THE INVENTION

1. Field of the Invention

The present invention relates to hair care compositions containing a combination of a selected amine and/or a quaternized amine, especially an amidoamine and/or quaternized amidoamine, and a terminal functionalized diquaternary silicone compound.

2. Description of the Related Art

The trend in hair care products is to provide the best possible care ("hair consciousness"). The users of hair treatment compositions are often concerned that their hair is strongly affected by hair treatment agents, such as permanent wave composition or dye compositions, or by the environment. Care products must help care for the hair, especially damaged hair, but at the same time the hair must appear natural, i.e. not loaded. Good care can of course be obtained with conventional hair care compositions for damaged hair (e.g. by dimethicone in various formulae), however they load the hair. The requirements or demands on cosmetic care compositions in regard to their many properties and environmental friendliness of their active ingredients are always increasing. The requirements that the care compositions should provide optimum care properties without producing undesirable effects on the user and an undesirable load on the environment are entirely decisive in determining whether or not a particular composition is selected or marketed. Also the care composition should increase the luster of the hair. Moreover these compositions must have sufficient stability and must be easy to handle.

The cationic surfactant, distearyldimethylammonium chloride (DSDMAC, INCI-name: Quaternium-18) is a known highly effect cationic care material. Especially it is contained in spray care compositions and foam care compositions. DSDMAC was widely used in the past in hair care compositions and today, above all, is used in treatments, which especially have care action (good care, little loading), and primarily in connection with polymeric silicone compounds. The primary disadvantage of these substances is that they are poorly biologically degradable. Moreover they have a highly aquatic toxicity and strongly load the environment. If DSDMAC were to be replaced by other conventional quaternary compounds, such as monoalkylquats (cetyltrimethylammonium chloride) or so-called ester quats, the highly effective application properties of the DSDMAC are not achieved.

On the other hand, cationic surfactants cannot be avoided in hair care compositions. In this connection the problem is that, in the case of liquid spray or foam cosmetic compositions, on the one hand, they must have a low viscosity and, on the other, they must form a stable emulsion. The use of, e.g., distearyldimethyl ammonium chloride or analogous quaternary ammonium compounds of course fulfills these conditions, however the use of these compounds in cosmetic compositions is no longer considered appropriate because of the above-described disadvantages.

WO 00/45787 describes hair care compositions characterized by containing a combination of at least one ester of an aliphatic, linear or branched carboxylic acid with a primary or secondary, branched or unbranched alcohol and an amine and/or a quaternized amine of the following formulae Ia and Ib:

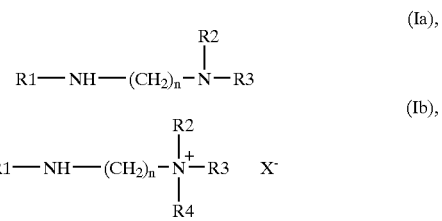

wherein R1 represents an acyl or alkyl group having 8 to 24 carbon atoms, which can be branched or unbranched, saturated or unsaturated, and wherein the acyl group and/or the alkyl group can contain at least one OH group;
wherein R2, R3 and R4 each represent, independently of each other, hydrogen or an alkyl group with from 1 to 4 carbon atoms, which can be saturated or unsaturated; X$^-$ is an anion and n is a whole number from 1 to 10.

These hair care compositions are however not completely satisfactory in meeting all the requirements.

SUMMARY OF THE INVENTION

It is an object of the present invention to provide a hair care composition having improved care properties, especially the feel and combability of the treated hair in the moist and dry state as well as a reduced load on the hair.

This object is attained in a hair care composition according to the invention containing a combination of (A) at least one amine of formula Ia, R1—NH—(CH$_2$)$_m$—NR2R3, and/or at least one quaternized amine of formula Ib, R1—NH—(CH$_2$)$_m$—N$^+$R2R3R4 X$^-$,
  wherein R1 represents an acyl or alkyl group having 8 to 24 carbon atoms, which can be branched or unbranched, saturated or unsaturated, and
  wherein the acyl group and/or the alkyl group can be substituted with or contain at least one OH group;
  wherein R2, R3 and R4 each represent, independently of each other, an alkyl group or an alkoxyalkyl group with from 1 to 6 carbon atoms, which can be saturated or unsaturated or substituted with one or more hydroxy groups or not substituted; X$^-$ is an anion and n is a whole number from 1 to 10; and (B) at least one terminally functionalized diquaternary silicone compound, especially at least one terminally functionalized diquaternary silicone polymer compound.

The hair care composition according to the invention provides both improved hair care and also reduces the load on the hair. This will be proven by means of the comparative experiments describe hereinbelow.

The cosmetic care composition according to the invention is a sprayable or foamable composition. It can be employed for all known cosmetic application, which relate to the hair. The hair care composition according to the invention, for example, especially is in the form of a spray care composition, a foam care composition, a rinse or a treatment. The hair care composition according to the invention can either be rinsed from the hair after a suitable acting time or can be left on the hair after application on the dry, moist or wet hair. The acting time depends on the type of hair. As a general guideline, the acting time can be between 0.5 to 30 minutes, especially between 0.5 and 10 minutes, preferably between 1.0 and 5.0 minutes.

Surprisingly a cosmetic hair care composition, preferably a liquid hair care composition, prepared with a combination of an amine and/or a quaternized amidoamine of the general formulae (Ia) and/or (Ib) and a terminal functionalized diquaternary silicone compound is suitable in an outstanding manner. This composition provides outstanding improved hair care properties. Surprisingly also the load on the hair produced with this hair care composition is not only not increased (which is usually the case when care action is improved), but is even reduced.

DESCRIPTION OF THE PREFERRED EMBODIMENTS

Hair care compositions according to the invention are preferred, in which the amines and/or the quaternized amines of the formulae (Ia) and/or (Ib) are amidoamines and/or quaternized amidoamines, wherein R1 represents a branched or unbranched, saturated or unsaturated acyl group with 8 to 24 carbon atoms, which can optionally contain at least one OH group.

Those amines and/or quaternized amines are preferred for the combination according to the invention, in which R1 in the formulae (Ia) and/or (Ib) is a fatty acid group, especially derived from an oil or wax, preferably a natural oil or wax. Lanolin, beeswax and candellila wax are examples that should be considered.

Also those amines and/or quaternized amines are preferred, in which at least one of the groups R2, R3 and R4 of the formulae (Ia) and/or (Ib) represent a group of the general formula, —CH$_2$CH$_2$OR5, wherein R5 can have the significance of an alkyl group with 1 to 4 carbon atoms, hydroxyethyl or H. The preferred size of n in the general formulae (Ia) and/or (Ib) is a number between 2 and 5.

Amines and/or quaternized amines of the general formula (Ia) and/or (Ib) are preferred, in which the anion X$^-$ is a halogenide or a compound of general formula RSO$_3^-$, wherein R has the significance of a saturated or unsaturated alkyl group with one to four carbon atoms and the alkyl groups can contain one or more hydroxyl groups.

Amines or aminoamines used in the compositions according to the invention, which can be optionally quaternized, for example, include REWOQUAT RTM 50 (Witco Surfactants GmbH, INCI-name: castor oil amidotrimonium methosulfate), Witcamine 100 (Witco, INCI-name: cocoamidopropyl dimethylamine), Incromine BB (Croda, INCI-name: behenamidopropyldimethylamine), Mackine 401 (McIntyre, INCI-name: isostearylamidopropyldimethylamine) and other Mackine types, Adogen S18V (Witco, INCI-name: stearylamidopropyldimethylamine), Empigen CSC (Albright & Wilson, INCI-name: Cocoamidopropyltrimonium chloride), Swanol Lanoquat DES-50 (Nikko, INCI-name: Quaternium-33), REWOQUAT UTM 50 (Witco, Surfactants GmbH, Undecyleneamido-propyltrimonium methosulfate).

The amines or quaternized amines in the hair care compositions according to the invention of the general formula (Ia) and (Ib) can be used individually, or in arbitrary combinations with each other. The hair care compositions of the invention contain from 0.01 to 10.0 percent by weight, especially between 0.01 and 5.0 percent by weight, of these amines or quaternized amines.

Suitable diquaternary silicone polymer compounds are selected from the silicone compounds of the general formula II:

R$^1$R$^2$R$^3$N$^+$—A—SiR$^7$R$^8$—(O—SiR$^9$R$^{10}$)$_n$—O—SiR$^{11}$R$^{12}$—A—N$^+$R$^4$R$^5$R$^6$2X$^{\prime -}$ (II), wherein R$^1$ to R$^6$, independently of each other, each represents an unsubstituted C1-alkyl group to C22-alkyl group or a substituted C1-alkyl group to C22-alkyl group with at least one hydroxy group; and wherein R$^7$ to R$^{12}$, independently of each other, are the same or different and each represent an unsubstituted C1-alkyl to C10-alkyl group or a phenyl group, A represents a divalent organic compound group, n a number from 0 to 200, preferably from 10 to 120, especially preferably from 10 to 40 and X$^-$ is an anion. The divalent compound group A is preferably a C1- to C12-alkylene or alkoxyalkylene group, which can optionally be substituted with one or more hydroxy group. The group —(CH$_2$)$_3$—O—CH$_2$—CH(OH)—CH$_2$— is especially preferred. The anion X$^-$ can be a halogen ion, an acetate, an organic carboxylate or a compound of the general formula RSO$_3^-$, wherein R has the significance of a C1-alkyl to C4-alkyl group.

The preferred diquaternary silicone polymer compounds have the general formula III:

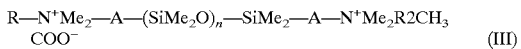
(III)

wherein A is the —(CH$_2$)$_3$—O—CH$_2$—CH(OH)—CH$_2$— group, R is an alkyl group with at least eight carbon atoms and n is a number from 10 to 120.

Suitable silicone polymer compounds with two terminal quaternary ammonium groups are known under the INCI name, Quaternium-80. They are dimethylsiloxanes with two terminal trialkylammonium groups. These diquaternary polydimethylsiloxanes are marketed by Goldschmidt under the trademark Abil® Quat 3270, 3272, 3474.

The care compositions according to the invention can include from 0.01 to 10.0 percent by weight, preferably from 0.1 to 5.0 percent by weight, of the diquaternary silicone compounds, especially polymer compounds.

The hair care compositions according to the invention preferably additionally include at least one ester of an aliphatic, linear or branched carboxylic acid with a primary or secondary, branched or unbranched alcohol and/or at least one additional silicone compound selected from the group consisting of alkyl siloxanes, alkylarylsiloxanes and aminosilicones, in order to provide further improvement of the hair conditioning properties. The ester can be contained in the care composition in an amount of 0.01 to 20.0 percent by weight, preferably of 0.01 to 10.0 percent by weight and especially preferably in an amount of from 0.01 to 5.0 percent by weight. The silicones and/or aminosilicones can be used as individual ingredients or in combination with each other in a total concentration of from 0.01 to 10.0 percent by weight, preferably in a concentration of from 0.01 to 8.0 percent by weight.

The advantageous properties of the esters of the carboxylic acids are especially obtained with esters of aliphatic linear or branched C8- to C18-carboxylic acids. As a result a hair care composition according to the invention is preferred in which the additional esters are esters of aliphatic linear or branched carboxylic acid groups having 8 to 18 carbon atoms. The branched or unbranched alcohol esterified with the carboxylic acid preferably has from one to six carbon atoms. The primary or secondary branched or unbranched alcohol for the esterification is preferably a monovalent alcohol. Isopropyl myristate is an entirely especially preferably carboxylic acid ester.

Suitable aminosilicone compounds include those with the INCI names, amodimethicone and trimethylsilylamodimethicone. The additional silicone compounds can be aminosilicones of the general formula IV:

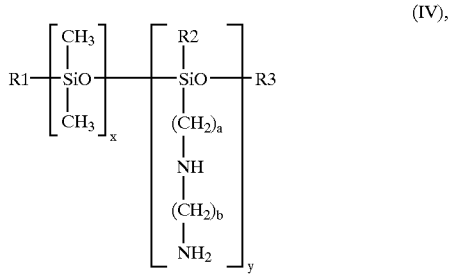

(IV), wherein R1 and R2 represent methyl or OH, R3 represents trimethylsilyl or H, a represents a whole number between 1 and 8, b represents a whole number between 1 and 5 and x and y represent an arbitrary numerical value. Especially aminofunctional silicones according to formula (IV), in which a represents a whole number between 2 and 4 and b represents a whole number between 1 and 3 are especially suitable.

These aminofunctional silicones have a molecular weight of 2000 to 100,000 and can, for example, be obtained from Dow Corning under the tradename, Silicone Emulsion No. 929, which has a content of aminofunctional silicones (R1, R2=OH, R3=H) of about 35%. Similarly, for example, an aminofunctional silicone of Toshiba with a tradename XF42-B1989 can be used in the composition according to the invention. This type of silicone is especially preferred in the care composition according to the invention.

Additional preferred aminofunctional silicones, which can be used for the hair care compositions according to the invention, include silicone compounds according to the structural formula V:

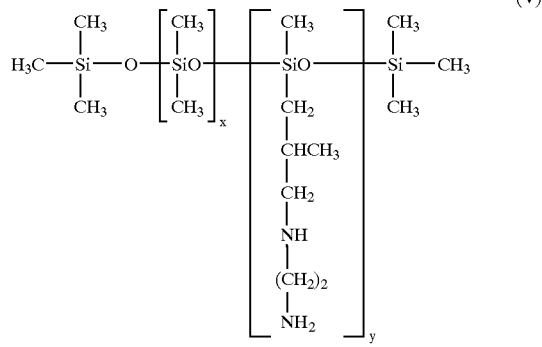

(V)

wherein the ratio x to y can vary between about 27.5:1 to about 160:1. The molecular weight of these compounds can be between 5000 and about 30,000. A product of this formula is marketed by Dow Corning under the tradename amodimethicone Q2-8075, which has a molecular weight of 8000 and a ratio of x to y of about 49:1. This amodimethicone is contained in the named product at about 37%.

The hair care composition according to the invention advantageously contains the silicone compounds of the general formula VI as additive ingredients:

(R1)$_2$R2Si—O—(Si(R1)$_2$—O)$_n$SiR2(R1)$_2$ (VI), wherein R1 represents methyl or OH, R2 represents methyl or phenyl and n represents a whole number.

The compounds of the general formula (VI) should preferably have viscosity of 1000 to 1,000,000 cSt at 25° C. Emulsions of silicone compounds, which for example are marketed by Toshiba under the tradename XS65-B3803, are especially suitable. These emulsions contain a silicone compound according to the general formula (VI) with a viscosity of about 100,000 cSt (active content about 30%). Further examples include the silicones marketed by Toray and named BY 22-050A, BY22-060, BY22-062 and/or BY22-047.

The hair care composition according to the invention can have a consistency providing agent added to it. The following additive ingredients are suitable consistency providing agents: fatty alcohols, especially those with 8 to 18 carbon atoms, preferably cetyl or cetearyl alcohol, as well as reaction products of these fatty alcohols with 1 to 10 Mol ethylene oxide or propylene oxide or their mixtures, cellulose or its derivatives, such as e.g. alkylhydroxyalkylcelluloses, especially Tylose C-type of Clariant, methylhydroxyethylcellulose, especially Tylose MH-type of Clariant, hydroxyethyl cellulose, for example Tylose H-type of Clariant or Natrosol 250 type of National Starch, hydroxypropylmethylcellulose, for example methocel type of Dow Chemical, silica and the so-called "hydrated silica", which for example is marketed by Degussa under the trademark Aerosil® or Sipernat®, or neutral polymer compounds, such as long chain polyvinyl pyrrolidone (PVP). Generally the consistency providing agent can be contained in the finished hair care composition in a concentration of from 0.1 to 15.0 percent by weight, preferably in a concentration of from 0.1 to 10.0 percent by weight in relation to the total amount of the hair care composition.

It has been shown that the hair care composition according to the invention provides additional advantageous hair care action when at least one cationic surfactant is added. The cationic surfactant can be used in an amount of from 0.01 to 5.0 percent by weight, preferably in an amount of from 0.1 to 3.0 percent by weight in relation to the total amount of the hair care composition according to the invention. According to the invention a cationic surfactant of the general formula $R^1R^2R^3R^4N^+$ $X^-$ can be used, in which $X^-$ is any cosmetically compatible anion, preferably chloride or methosulfate and the groups R1 to R4 are the same or different and are branched or unbranched alkyl groups with 1 to 22 carbon atoms, which can contain at least one hydroxyl group and wherein at least one of the groups R1 to R4 has at least eight carbon atoms, or one group is —(CH$_2$)$_n$—OC(=O)—R5, in which R5 is a saturated or unsaturated, branched or unbranched C8- to C22 alkyl group, which can contain one or more hydroxy group, and n is a whole number between 1 and 4. Compounds in which R1 and R2 are C8- to C22-alkyl group and in which R3 and R4 are C1-alkyl groups to C4-alkylgroups (DSDMAC type) are especially preferred.

For example, cetyltrimethylammonium chloride (Ardquad 16 of Akzo Nobel) or also so-called esterquats, whose manufacture is described in the European Patent Applications EP 0 284 036 A2, EP 0 669 391 A2 and EP 0 550 361 A1, are preferred compounds. Their use for care of keratinic and other fibers is described in International Patent Application WO 96/03970 A1 and European Patent Application EP 0 636 356 A1, EP 0 689 532 A1 and EP 0 614 349 A1. The compounds are, for example, sold under the trademarks REWOQUAT® WE 18, REWOQUAT® WE 38 DPG (Witco Surfactants GmbH), STEPANTEX® GS 90 (Stepan), ARMOCARE® VGH-70 (Akzo Nobel) or DEHYQUART® L-80 (Henkel).

Also the so-called betaine esters can be used in the usual amounts, as described in the German Patent Application DE 35 27 974 A1, in the hair care compositions according to the invention.

Understandably the hair care compositions according to the invention can contain all of the known and conventional cosmetic auxiliary, effective and/or additive ingredients. One skilled in the art knows how these auxiliary and/or effective and/or additive cosmetic ingredients are employed in hair and skin cosmetic compositions, so that the more detailed description that follows is only exemplary in character. It should be considered as serving only for further illustration of the present invention. The following literature references can be pointed out, which describe the general composition of hair care compositions: K. SCHRADER, Foundations and Formulation of Cosmetics, 2nd Edition, 1989, pp. 728 to 727 or A. DOMSCH, COSMETIC PREPARATIONS, Chemical Industry Press (Verlag für chemishche Industrie), (H. Ziolkowsky, Ed.), 4th Edition, Volume 2, pp. 212 to 230, 1992 or D. H. JOHNSON (Editors), Hair and Hair Care, New York, 1997, pp. 65 to 104. The additive, auxiliary and carrier ingredients can be employed in conventional amounts known to one skilled in the art, for example especially in amounts of from 0.1 to 10 percent by weight.

The following conventional cosmetic auxiliary, effective and/or additive ingredients, which can be employed in the hair care compositions according to the invention, can be listed as examples of suitable cosmetic auxiliary, effective and/or additive ingredients: nonionic polymers, vegetable and mineral fats and oils, perfume oils, dyestuffs common in hair cosmetics, additional hair conditioning ingredients, such as synthetic and natural phospholipids, quaternary derivative compounds, such as starches or cellulose, solvating agents, for example short chain primary and secondary alcohols (for example ethanol, 1-propanol or 2-propanol), proteins or protein derivatives, for example protein hydrolyzates (such as collagen hydroyzates, keratin hydrolyzates, silk protein hydrolyzates or wheat protein hydrolyzates), amino acids and their derivatives (for example histidine, glycine, alanine, serine, threonine, arginine, cysteine and their derivative compounds, for example with fatty acid condensation products), vegetable extracts, vitamins or provitamins (for example biotin, vitamin C, D-panthenol and derivatives thereof), allantoin, chitosan, viscosity-regulating substances, such as fatty acid alkanol amides, alkoxylated esters of polyols (for example glycerol, sorbitol, fructose, or glucose), anti-flaking agents, inorganic or organic acids (such as acetic acid, lactic acid, citric acid, glycolic acid, malic acid, phosphoric acid), sun protective agents, and/or UV absorbers, preservatives, antioxidants (for example tocopherol or its esters).

The following cationic or water-soluble, nonionic polymers are suitable in the compositions according to the invention: above all polydialkyldiallyl ammonium compounds, polyvinyl pyrrolidone, copolymers of vinyl pyrrolidone and dialkylaminoalkylmethacrylates or quaternary copolymers of vinyl pyrrolidone and dialkylaminoalkylmethacrylates, such as dimethyldiallyl ammonium chloride polymers (Merquat 100 (Calgon), Polyvinylpyrrolidone (Luviskol K 80 (BASF)), copolymers of vinyl pyrrolidone and dimethylaminoethylmethacrylates (Copolymer 845, Copolymer 937, Copolymer 958 of ISP) with diethyl sulfate quaternized copolymers of vinyl pyrrolidone and dimethylaminoethyl methacrylates (Gafquat 734, Gafquat 755 N or Luviquat PQ 11).

The pH value of the hair care compositions according to the invention is in the neutral range to acid range, preferable between 2.0 and 6.0. The pH value can be adjusted with a known adjusting agent. Inorganic or organic acids are suitable for this purpose, especially phosphoric acid, citric acid, lactic acid, malic acid, glycolic acid or acetic acid.

The hair composition according to the invention can be present in any application form known for liquid hair care compositions, for example as a spray care composition, as a rinse, as a foam care composition or treatment. The hair care composition according to the invention can remain in the hair after application or be rinsed from it. A hair care composition, which is rinsed out of the hair, is preferred.

The hair care composition according to the invention can—after its viscosity is adjusted—advantageously be sprayed or foamed with the help of a conventional pumping or metering devices onto dry or moisture hair, for example as an aerosol. Suitable spraying or foaming devices are known to one skilled in the art. These devices can be operated with a propellant or with a mechanically caused pressurizing means. Application occurs preferably in connection with washing the hair.

When the hair care composition according to the invention is to be applied with the help of a propellant, especially when it is sprayed or foamed, it can be filled together with a conventional propellant in a suitable pressurized container, especially into an aerosol can, in the conventional ratios or amounts. For example, a ratio of hair care composition to propellant such as 92:8 is suitable. The interior pressure depends on the container that is used. As a guideline pressures in a range from 1.5 to 8.0 bar at a temperature of 20° C. are typically produced. For example, suitable propellants include lower alkanes, such as n-butane, i-butane and propane, dimethyl ether, and gaseous propellants, for example $N_2$, $N_2O$ or $CO_2$, as well as mixtures of the foregoing propellants.

The mechanical spraying or foaming devices include those devices, which produce a spray or foam without using a propellant. Suitable mechanical spraying or forming devices, for example, can include a pump or an elastically deformable container with a spray valve, in which the hair care composition according to the invention is filled. In case the filling occurs under pressure the hair care composition according to the invention is dispensed continuously after opening the spray or foam valve. Alternatively it is dispensed in metered amounts by operation of the spray or foam valve. In other cases the pressure required for dispensing the composition according to the invention is produced by reversible mechanical deformation of the container.

Based on the outstanding properties of the combination of an amine and/or quaternized aminoamine and at least one terminal functionalized diquaternary silicone polymer according to the invention, cosmetic preparations, which have excellent care and/or cleansing and/or conditioning properties, especially by forming a coating, can be manufactured. For example the combination according to the invention can be used for manufacture of mascara preparations, eye brow preparations, hair styling compositions, hair conditioning compositions, hair shaping compositions, hair dye compositions, hair pre-treatment compositions and hair after-treatment compositions, tonics and/or hair water or deodorants. The present invention also includes methods of making cosmetic preparations with the combination with an amine and/or a quaternized amine and at least one terminal functionalized diquaternary silicone according to the above description. The present invention comprises cosmetic preparations containing a combination of an amine and/or a quaternized amine with at least one terminal functionalized diquaternary silicone compound. The hair care composition according to the invention is illustrated in further detail by the example set forth hereinbelow.

EXAMPLE

Compositions A to C according to the invention and comparative compositions D to F are described below in Table I. The numbers in Table I below are weight percentages, in relation to the total amount of the composition, of the ingredients listed on the left hand side of Table I. Comparative hair treatment tests were made in which the compositions of the invention were compared with the comparative compositions, which are not of the invention. First the hair to be treated was washed with a commercially available mild shampoo without conditioning or care action. Then the test product was applied to the hand towel dried hair. The product was against rinsed out of the hair after about three minutes acting time. A panel of experts judged the hair quality of hair treated the compositions of the invention in half side tests, which facilitated an accurate comparison. The observed results of the half side tests are shown in Table II. The results of treating one half of the hair on the head of a test subject with a composition of the invention and the other half with a corresponding comparative composition were rated as either better or poorer by the panel of experts.

TABLE I

COMPOSITIONS A TO C OF THE INVENTION AND COMPARATIVE COMPOSITIONS D TO F

| INGREDIENTS | A | B | C | D | E | F |
|---|---|---|---|---|---|---|
| Cetearyl alcohol | 6 | 6 | 8 | 6 | 6 | 8 |
| Paraffin | 4 | 4 | — | 4 | 4 | — |
| Lanolin | — | — | 2 | — | — | 2 |
| Lanoquat ® DES-50[4] | 1 | — | 1 | 1 | — | 1 |
| REWOTERIC ® RTM 50[5] | — | 1 | — | — | 1 | — |
| Isopropyl myristate | 4 | 2 | 2 | 4 | 2 | 2 |
| Quat. Organo-silicone[1] | 1 | 1.5 | 1 | — | — | — |
| TMS-amodi-methicone[2] | 0.8 | — | 1.3 | 0.8 | — | 1.3 |
| TMS-amodi-methicone emulsion[3] | — | 1 | — | — | 1 | — |
| Cetyltrimethyl Ammonium chloride | 2 | 1.3 | 1.3 | 2 | 1.3 | 1.3 |
| Dimethicone | | | | | | 1 |
| Perfume | 0.1 | 0.1 | 0.1 | 0.1 | 0.1 | 0.1 |
| Citric acid | To pH4 | To pH4 | To pH4 | To pH4 | To pH4 | To pH4 |
| Water | To 100 | To 100 | To 100 | To 100 | To 100 | To 100 |

[1]Abilquat ® 3272 of Goldschmidt
[2]100% Toshiba XF 49-B1989
[3]Dow Corning 939
[4]Quaternium-33, quaternary amidoammonium salt on the basis of lanolin
[5]Castor oil amidopropyltrimonium methosulfate

TABLE II

RESULTS OF HALF-SIDE TESTS COMPARING COMPOSITIONS ACCORDING TO THE INVENTION WITH THOSE OF THE PRIOR ART

| | Feel Moist | Combability Moist | Feel Dry | Combability Dry | Load |
|---|---|---|---|---|---|
| A vs. D | A better | A better | A better | A better | A less |
| B vs. E | B better (smoother) | B better | B better (smoother) | B better | B less |
| C vs. F | C better | C better | C better (softer) | C better | C less |

By definition an "unsaturated alkyl radical or group" means a univalent hydrocarbon group that has at least some unsaturation, i.e. at least one double or triple bond.

By definition an "unsaturated acyl radical or group" means a univalent group or radical derived by removing an OH group from an organic acid that has at least some unsaturation, i.e. at least one double or triple bond.

By definition an "unsaturated alkoxyalkyl radical or group" means a univalent hydrocarbon group that has at least some unsaturation, i.e. at least one double or triple bond.

The disclosure in German Patent Application 10104033.4 of Jan. 31, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in hair care compositions with diquaternary silicone polymers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. The hair care composition comprising:

from 0.01 to 10 percent by weight of at least one terminally functionalized diquaternary silicone compound of formula II:

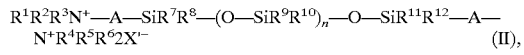
   $$R^1R^2R^3N^+\text{---}A\text{---}SiR^7R^8\text{---}(O\text{---}SiR^9R^{10})_n\text{---}O\text{---}SiR^{11}R^{12}\text{---}A\text{---}N^+R^4R^5R^6 2X'^- \quad \text{(II)},$$

wherein $R^1$ and $R^4$, independently of each other, each represent an alkyl group with at least eight carbon atoms, and $R^2$ $R^3$ and $R^5$ to $R^{12}$, independently of each other, each represent a methyl group, A represents —$(CH_2)_3$—O—$CH_2$—$CH(OH)$—$CH_2$—, n is a number from 10 to 120 and $X'^-$ is an anion; and from 0.01 to 10 percent by weight of at least one quaternized amine compound of formula Ib:

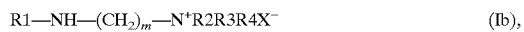
   $$R1\text{---}NH\text{---}(CH_2)_m\text{---}N^+R2R3R4X^- \quad \text{(Ib)},$$

wherein R1 represents a C8- to C24-acyl group;

wherein R2, R3 and R4 represent, independently of each other, a C1- to C6-alkyl group $X^-$ is an anion and m is 3.

2. The hair care composition as defined in claim 1, wherein said $X^{31}$ is a halogen anion or $RSO_3^-$, wherein R represents a C1- to C4-alkyl group or an unsaturated C1- to C4-alkyl group.

3. The hair care composition as defined in claim 1, wherein said $X'^-$ is a halogen anion, an acetate anion, an organic carboxylate anion or $R'SO_3^-$, wherein R' is an unsubstituted C1-alkyl to C4-alkyl group.

4. The hair care composition as defined in claim 1, further comprising at least one member selected from the group consisting of esters of aliphatic carboxylic acids with pri mary alcohols, esters of aliphatic carboxylic acids with secondary alcohols, alkyl siloxanes, alkylaryl siloxanes and aminosilicone compounds.

5. The hair care composition as defined in claim 1, further comprising at least one cationic surfactant.

6. The hair care composition as defined in claim 5, wherein said at least one cationic surfactant is of formula $R^{13}R^{14}R^{15}R^{16}N^{30}\ Y^-$, wherein $Y^-$ is an anion and said $R^{13}$, $R^{14}$, $R^{15}$ or $R^{16}$ each represent, independently of each other, an unsubstituted C1-alkyl to C22-alkyl group or C1-alkyl to C22-alkyl group substituted with at least one hydroxy group, at least one of said $R^{13}$, $R^{14}$, $R^{15}$ and $R^{16}$ has at least eight carbon atoms or is $-(CH_2)_p-OC(=O)-R_{17}$, wherein $R^{17}$ is an unsubstituted C8-alkyl to C22-alkyl group or a C8-alkyl to C22-alkyl group substituted with at least one hydroxy group and p is a number between 1 and 4.

\* \* \* \* \*